United States Patent [19]

Moon et al.

[11] Patent Number: 5,100,909
[45] Date of Patent: Mar. 31, 1992

[54] ACETYLENIC IMIDAZOLES HAVING CENTRAL NERVOUS SYSTEM ACTIVITY

[75] Inventors: Malcolm W. Moon; Richard F. Heier, both of Kalamazoo, Mich.

[73] Assignee: The Upjohn Company, Kalamazoo, Mich.

[21] Appl. No.: 635,569

[22] Filed: Jan. 22, 1991

Related U.S. Application Data

[63] Continuation of Ser. No. 223,576, Jul. 25, 1988, abandoned.

[51] Int. Cl.⁵ ............... A61K 31/415; A61K 31/445; C07D 403/12; C07D 401/12
[52] U.S. Cl. ..................... 514/397; 514/326; 514/399; 546/210; 548/336; 548/337; 548/341
[58] Field of Search ............ 548/336, 337, 341; 546/210; 514/397, 399, 326

[56] References Cited

U.S. PATENT DOCUMENTS

| | | | |
|---|---|---|---|
| 3,925,411 | 12/1975 | Dahlbom | 548/524 |
| 3,959,311 | 5/1976 | Dahlbom | 540/602 |
| 4,463,001 | 7/1984 | Melloni et al. | 548/336 X |
| 4,721,783 | 1/1988 | Davis | 548/341 X |

FOREIGN PATENT DOCUMENTS 0117462 5/1984 European Pat. Off. .
0127727 12/1984 European Pat. Off. .

OTHER PUBLICATIONS

Press et al., *J. Med. Chem.*, 29, 816-819 (1986).
Ringdahl, B., *J. Med. Chem.* 31, No. 3, 683-688 (1988).
Nilsson, et al, *J. Med. Chem.*, 31 No. 3, 577-582 (1988).

*Primary Examiner*—Mary C. Lee
*Assistant Examiner*—Lenora Miltenberger
*Attorney, Agent, or Firm*—Donald Corneglio

[57] ABSTRACT

Acetylenic imidazole compounds having cholinergic agonist or antagonist activity useful in the treatment of mental disorders, extrapyramidal motor disorders, disorders of the parasympathetic nervous system and glaucoma or as analgesics for the treatment of pain. Typical central nervous system disorders for which the subject compounds can be used include cognitive disorders of all ages, including senile dementia, Alzheimer's disease and other related disorders. The compounds are particularly developed to improve mental performance when a mental deficiency is diagnosed.

16 Claims, No Drawings

ACETYLENIC IMIDAZOLES HAVING CENTRAL NERVOUS SYSTEM ACTIVITY

This application is the national phase of international application PCT/US89/02537, which is a continuation of Ser. No. 07/223,576, filed July 25, 1988, now abandoned.

BACKGROUND OF THE INVENTION

The present invention is directed toward acetylenic imidazole compounds having central nervous activity. The compounds exhibit cholinergic agonists activity and are particularly useful for improving mental performance, glaucoma or treating mental deficiencies. As an example, Alzheimer's disease is a congenitive disorder characterized in part by a significant reduction in choline acetyltransferase activity, high affinity choline uptake and synthesis of acetylcholine in the forebrain areas which receive cholinergic input. The reduction in presynaptic markers of the forebrain cholinergic neurons is due to the degeneration of these neuronal pathways. Clinical observations indicate that the central cholinergic system may be involved in the physiology of cognitive functions. Thus there is a medical need for a cholinergic agonist which is likely to have therapeutic efficacy in cognitive disorders. Cholinergic agonists can also be useful as analgesics to treat pain.

Those compounds having cholinergic antagonist activity are useful in the treatment of extrapyramidal motor disorders. The central nervous system activity of the compounds also indicates that they can be useful in the treatment of disorders of the parasympathetic nervous system.

These compounds are related to cholinergic agonists oxotremorine [N-(4-pyrrolidino-2-butynyl)-pyrrolidin-2-one], which induces tremors and spasticity in laboratory animals by a cholinergic mechanism at extremely low doses. These undesirable side effects prevent the use of oxotremorine as a drug, and considerable effort has been directed to the preparation of related, clinically useful cholinergic agonists and antagonists.

DESCRIPTION OF RELATED ART

U.S. Pat. No. 3,925,411 discloses an oxotremorine antagonist N-(5-pyrrolidino-3-pentynyl)-pyrrolidin-2-one which is reported to have an increased half life over prior oxotremorine compounds. U.S. Pat. No. 3,959,311 also discloses compounds related to oxotremorine which are agonists, partial agonists and antagonists on isolated guinea pig ileum. These compounds are reported to have greater potency and less side-effects (antagonizing peripheral cholinergic effects) than the prior art compounds. Despite the proliferation of oxotremorine-like compounds there has been a continuing need to find more effective and safe compounds for treating mental disorders, extrapyramidal motor disorders, disorders of the parasympathetic nervous system and glaucoma.

More recently, a series of actylenic amine compounds have been developed and evaluated for potential value in treating neurological and psychiatric conditions. A series of N-(4-amino-2-butynyl)-5-methyl-2-pyrrolidones were reported in Ringdahl, B, "5-methyl-2-pyrrolidone Analogues of Oxotremorine as Selective Muscarinic Agonists, J. Med. Chem. 31, 683–688 (1988). Another series of tertiary and quaternary analogues of N-methyl-N-(1-methyl-4-pyrrolidino-2-butynyl) acetamide were reported to have central antimuscarinic activity as they antagonized oxotremorine-induced tremors in mice as reported in Nilsson, et al., "Derivatives of the Muscarinic Agent N-methyl-N-(1-methyl-4-pyrrolidino-2-butynyl)acetamide", J. Med. Chem., 31, 577–582 (1988).

SUMMARY OF THE INVENTION

The present invention is directed toward a family of acetylenic imidazole compounds having central nervous system activity. The compounds are represented by structural Formula I shown on the Formula sheet below or a therapeutically acceptable salt thereof, wherein X is $H_2$ or O; $R_1$ is hydrogen, methyl, ethyl, methylamino, dimethylamino, methoxy or ethoxy; $R_2$ is hydrogen, methyl or ethyl or $R_1$ and $R_2$ are joined to form a cyclic ring which can be methyl and/or carbonyl substituted; and $R_3$, $R_4$ and $R_5$ are independently choosen from hydrogen, methyl or ethyl or a halogen (fluorine, chlorine, bromine and iodine).

The invention further provides a method for improving mental performance, treating pain, extrapyramidal motor disorders, glaucoma or parasympathetic nervous system disorders in animal or human hosts by administering a pharmaceutically effective amount of the subject compound.

DETAILED DESCRIPTION OF THE INVENTION

The new compounds of the present invention are structurally depicted by Formula I wherein X is $H_2$ or O; $R_1$ is hydrogen, methyl, ethyl, methylamino, dimethylamino, methoxy or ethoxy; $R_2$ is hydrogen, methyl or ethyl or the $R_1$ and $R_2$ groups can be joined to form various cyclic structures such as pyrrolidone, pyrrolidinone, piperidine or piperidinone all of which can be optionally substituted with a lower alkyl ($C_1$ to $C_5$,) preferably a methyl group or an additional carbonyl group. $R_3$, $R_4$ and $R_5$ are independently choosen from hydrogen, methyl or ethyl or a halogen. Preferably, $R_4$ is hydrogen or methyl and $R_5$ is hydrogen.

A series of acetylenic imidazoles as generically disclosed in Formula I were synthesized from three reaction schemes to form three more specific structures i–iii as shown on the Formula sheet below wherein R is a hydrogen, lower alkyl ($C_1$–$C_5$) group or an additional carbonyl group and the other R groups are as indicated above.

A compound of Structure i, 1-[4-(1H-imidazol-1-yl)-2-butynyl]-2-pyrrolidinone, is prepared by Scheme 1 as shown on the Scheme sheets below.

1-(2-propynyl)-3-pyrrolidinone, prepared from propargyl bromide and the potassium salt of pyrrolidinone, is reacted with paraformaldehyde and diethylamine using cuprous chloride as catalyst to give 1-[4-(diethylamino)-2-butynyl]-2-pyrrolidinone. This compound is reacted with cyanogen bromide to give 1-(4-bromo-2-propynyl)-2-pyrrolidinone (BPP) which is then reacted with excess imidazole to give 1-[4-(1H-imidazol-1-yl)-2-butynyl]-2-pyrrolidinone (Compound 1, shown in Table 1). It was essential to avoid the use of strong bases in this reaction, because when BPP is reacted with the potassium salt of imidazole the allene is yielded as the major product.

Analogues of compound 1 are prepared by the same reaction scheme using various imidazoles for reaction with BPP or alkyl substituted analogues of BPP such as those prepared from intermediate compounds 1-[4-(diethylamino)-2-butynyl]-5-methyl-2-pyrrolidinone, 1-[4-(diethylamino)-1-methyl-2-butynyl]-2-pyrrolidinone, and 1-[4-(diethylamino)-2-butynyl]-2,5-pyrrolidinedione to give the compounds shown in Table 1. Reaction of 4-methylimidazole, 2-methylimidazole, 2-ethylimidazole 2-chloroimidazole, 2,4- and 4,5-dimethylimidazole with BPP prepares compounds 2-4 and 7-9 shown in Table 1. For the synthesis of these analogues it is important to react BPP with the imidazole free base to avoid formation of allene by-products. In the reaction of 4-substituted-5-H-imidazoles with BPP a mixture of two isomeric products are formed and these may be separated by conventional means such as by chromatography or by fractional crystallization of the mixture as the free base or as a salt. Where the 5-substituted product of Structure i is desired, the product is more conveniently prepared by reacting BPP with a 1-acyl-4-substituted imidazole as outlined in Scheme 2 (see, Scheme sheets below) for the preparation of 1-[4-(5-methyl-1H-imidazol-1-yl)-2-butynyl]-2-pyrrolidinone.

The initial reaction product, an imidazolium salt, is conveniently crystallized to remove impurities and then solvolyzed to afford the desired product as the hydrobromide salt.

Structure ii compounds are prepared by the same procedures using the acetylenic diethylamine intermediates N-[4-(diethylamino)-1-methyl-2-butynyl]-N-methylacetamide, N-[4-(diethylamino)-2-butynyl]acetamide, N-(4-(diethylamino)-2-butynyl)-N-methylacetamide, [4-(diethylamino)-2-butynyl]trimethyl urea, and methyl [4-(diethylamino)-2-butynyl]methylcarbamate. The products obtained are shown in Table 2, compounds 14-27.

Structure iii compounds are prepared in two steps from imidazole or an alkyl substituted imidazole as illustrated in Scheme 3 (see Scheme sheets below) to produce 1-[4-(1H-imidazole-1-yl)-2-butynyl]pyrrolidine (Compound 28, Table 3).

Propargyl bromide is reacted with excess imidazole in THF, dioxane, or methanol to give 1-(2-propynyl)-1H-imidazole (PHI). PHI could also be prepared by reacting propargyl bromide with the potassium salt of imidazole in THF, but this procedure is less satisfactory as the product is contaminated with 1-(1,2-propadienyl)-1H-imidazole.

Reaction of PHI with paraformaldehyde and pyrrolidine using cuprous chloride as a catalyst gives 1-[4-(1H-imidazol-1-yl)-2-butynyl]pyrrolidine (28). Several analogues of this compound are prepared by the same reaction sequence from alkyl substituted imidazoles (30 and 32) and using the secondary amines dimethylamine (23) or diethylamine (29) in place of pyrrolidine (Table 3).

The compounds of the invention have central nervous system activity and therefore, are useful in the treatment of mental disorders such as senile dementia, Alzheimer's disease, schizophrenia, mania and depression, extrapyramidal motor disorders such as Parkinson's disease, Huntingtons chores, tardive dyskensia, disorders of the parasympathetic nervous system such as post-operative abdominal distension, gastric atony, irritable colon syndrome, colitis diverticulitis, biliary colic, peptic ulcers, urine retention and renal colic, or glaucoma or as analgesics for the treatment of pain.

Compounds useful for improving mental performance are recognized as cholinergic agonists or partial agonists. These compounds can also be useful as analgesics and for the treatment of glaucoma. The agonists are easily identified from cholinergic receptor binding results by calculating the Ki ratios. Any compound having a Ki ratio of at least ten is considered an agonist or partial agonist and, therefore, a pharmaceutical candidate for improved mental performance or as an analgesic. Whereas compounds having a Ki ratio less than ten are considered antagonist which are useful in the treatment of extrapyramidal motor disorders.

The activities of the new acetylenic amines of structure i are shown in Table 1 together with data for the related cholinergic agonist oxotremorine and the antagonists oxotremorine-5. The activities of compounds of structure ii and BM-5 are shown in Table 2. Compounds in Tables 1 and 2 include cholinergic agonists (compounds showing a Ki ratio (Ki QNB/Ki oxotremorine M) of $>100$, e.g. compound 1), cholinergic antagonists (Ki ratio $<10$), e.g. compound 2 and cholinergic partial agonists with intermediate Ki ratios (e.g. compound 3). Activities of compounds of Structure iii and tremorine are shown in Table 3. All of the Structure iii compounds show lower activity in the binding assays, but are more active when tested in mice.

The pharmacological activity for each of the compounds prepared is reported on the respective Tables 1-3. The biological methods employed were as follows:

Cholinergic receptor binding data for each of the compounds was obtained using the tritiated ligands oxotremorine M and quinuclidine benzylate.

Oxotremorine antagonist assays were performed on groups of six mice weighing 18-22 g. Each was dosed intraperitoneally with the test compound prepared in 0.25% methylcellulose and were placed in individual cages. Twenty minutes later the mice were injected subcutaneously with 0.5 mg/kg of oxotremorine dissolved in saline. Ten minutes later the mice were scored for body tremor. Doses of the compound under study began at 100 mg/kg and were decreased at a 0.5 log interval until no responders were obtained. The procedure described by Spearman and Karber, Finney, J. J., "Statistical Methods in Biological Assay", Chapter 20, was used to calculate the $ED_{50}$ and 95% confidence intervals.

For determination of analgesic activity, the test compound was injected subcutaneously into a group of four $CF_1$ mice. Thirty minutes later the mice were injected i.p. with 0.15% HCl, 10 ml./kg. Mice are then placed in plastic boxes and observed for fifteen minutes to record the number of animals failing to writhe. If at least three of the mice receiving the test compound failed to writhe, the compound was retested at does levels decreasing at 0.3 log intervals.

For antagonism of amnesia produced by scopolamine a one trial, step through passive avoidance paradigm was used. In this procedure a mouse was placed on a square platform adjoining darkened chamber. The mouse could enter the chamber through a hole above the platform. Following placement on the platform, the mouse was enclosed by a clear plexiglas cover which mildly restricted movement, limiting the animal to turning around and partial rearing. A sliding door was opened after this, exposing the entrance to the chamber. A timer was started at the same time the door was opened, in order to record latency to enter the chamber. Upon complete entry into the darkened box, the door was closed behind the mouse and a 1 mA, 2 sec, direct current shock applied to the feet of the mouse through the grid floor. The mouse was immediately removed from the chamber and returned to a 24 hr group holding cage.

Drug testing involved intraperitoneal injection of the test compound followed 15 min later by subcutaneous injection of 1 mg/kg scopolamine hydrobromide. Training was then conducted 15 min following scopolamine injection. Mice were housed in group cages overnight and tested for retention 24 hrs after training. Test sessions were conducted exactly like training sessions, except that no drugs were administered before testing and no shock was given upon entry. The latency for each mouse to enter the chamber was recorded, with a cut-off at 180 sec.

Median group latencies to enter the chamber during both training and testing were recorded and a Wilcoxon rank sum test applied to data comparing the parallel "scopolamine only" group with all drug combination groups on testing. On training, comparisons were made between the "No Drug" group, which received saline prior to shock training, and each of the scopolamine and test compound combinations.

Of the compounds tested using this procedure, compounds 15 and 24 were most active.

The dosage regiment for treating patients with the compounds of this invention is selected in accordance with a variety of factors including the type, age, weight, sec, and medical condition of the patient, the severity of the psychosis, the route of administration and the particular compound employed. An ordinarily skilled physician or psychiatrist will readily determine and prescribe the effective amount of compound to prevent or arrest the progress of the condition. In so proceeding, the physician or psychiatrist could employ relatively low dosages at first, subsequently increasing the dose until a maximum response is obtained.

Initial dosages of the compounds of the invention are ordinarily in the area of at least 10 mg up to about 1200 mg per day orally, which may be given in a single dose or in multiple doses. When other forms of administration are employed equivalent doses are administered. When dosages beyond 600 mg are employed, care should be taken with each subsequent dose to monitor possible toxic effects.

The compounds of this invention are administered in oral unit dosage forms such as tablets, capsules, pills, powders, or granules. They may also be introduced parenterally, (e.g., subcutaneously, intravenously, or intramuscularly), using forms known to the pharmaceutical art. They also may be administered rectally or vaginally in such forms as suppositories or bougies. In general, the preferred route of administration is oral.

The compounds of this invention can also be administered as therapeutically acceptable salt such as hydrochloride, hydrobromide, hydroiodide, sulfate, phosphate, acetate, propionate, lactate, maleate, malate, succinate, tartrate, cyclohexanesulfamates, methanesulfonates, ethanesulfonates, benzenesulfonates, toluenesulfonates and the like. Additionally, the compounds of this invention may be administered in a suitable hydrated form.

EXAMPLE 1

1-[4-(1H-Imidazol-1-yl)-2-butynyl]-2-pyrrolidinone (Compound 1)

Part A 1-(4-Bromo-2-butynyl)-2-pyrrolidinone

Cyanogen bromide (3.4 g, 0.032 mol) was added to a stirred solution of 1-(4-diethylamino-2-butynyl)-2-pyrrolidinone (6 g, 0.029 mol) in dioxane (60 mL). After stirring at room temperature for 10 min., the solvent was removed under reduced pressure to give 7.97 g of orange oil. The compound was purified by chromatography on silica gel in chloroform to give 1-(4-bromo-2-butynyl)-2-pyrrolidinone (5.2 g of orange oil) and N-ethyl-N-[4-(2-oxo-1-pyrrolidinyl)-2-butynyl]cyanamide (0.18 g of brown oil). Both products were characterized by NMR and mass spectral analysis.

Part B

1-[4-(1H-Imidazol-1-yl)-2-butynyl]-2-pyrrolidinone

Imidazole (3.4 g, 0.05 mol) was added to a stirred solution of 1-(4-bromo-2-butynyl)-2-pyrrolidinone (3.3 g, 0.015 mol) in THF (300 mL). After 3 days at room temperature the THF was removed under reduced pressure and the product was partitioned between ethyl acetate and 4N NaOH solution (5 mL). The ethyl acetate was removed and the residual oil was chromatographed on silica gel using chloroform as the initial eluant. Elution of the column with 2.5% methanol:chloroform gave 2.2 g of product as a liquid.

The bulk of the product was mixed with 1.1 g of anhydrous oxalic acid. Crystallization from methanol:ether gave 2.4 g of oxalate salt, m.p. 109°-115° C. Recrystallization from the same solvents gave 2.2 g, m.p. 115°-118° C.

EXAMPLE 2

1-[4-(2-Methyl-1H-imidazol-1-yl)-2-butynyl]-2-pyrrolidinone (Compound 2)

This product, a liquid, was prepared according to Example 1, part B, by substituting 2-methylimidazole for imidazole. The bulk of the product was converted to the oxalate salt, m.p. 81°-85° C.

EXAMPLE 3

1-[4-(5-Methyl-1H-imidazol-1-yl)-2-butynyl]-2-pyrrolidinone (Compound 3)

The 1-Acetyl-4-methylimidazole intermediate was prepared by making a mixture of 4-methylimidazole (82.1 g, 1.0 mol)) and acetic anhydride (190 mL, 2.0 mol) and refluxing for 15 min after which time 150 mL of solvent was removed by distillation at atmospheric pressure (head temperature 125° C.) over a 1 h period. The remaining acetic anhydride was removed at 50° C./0.5 mm and the residual liquid was crystallized from ether (150 mL) at −20° C. to give 85.5 g of 1-acetyl-4-methylimidazole product, m.p. 49°-51° C.

Part A

1-Acetyl-4-methyl-3-[4-(2-oxo-1-pyrrolidinyl)-2-butynyl)-imidazolium bromide

A mixture of 1-(4-bromo-2-butynyl)-2-pyrrolidinone (10.8 g, 0.05 mol) and 1-acetyl-4-methylimidazole (12.4 g, 0.10 mol)) in acetonitrile (20 mL) was heated in an oil bath (bath temperature 85° C.) for 1 h. The solution was diluted to 100 mL and cooled to −10° C. and the precipitate of imidazolium salt was filtered off and washed with acetonitrile:ether to give 7.8 g of product, m.p. 174°-177° C.

Part B

1-[4-(5-Methyl-1H-imidazol-1-yl)-2-butynyl]-2-pyrrolidinone hydrobromide

The imidazolium salt (6.0 g) was dissolved in methanol (100 mL). After 2 h the solvent was removed and the residual solid was reconstituted in methanol (20 mL) and ether (15 mL) was added. The solution was filtered and the precipitate was washed with methanol:ether (1:10) to give 4.9 g (97%) of 1-[4-(5-methyl-1H-imidazol-1-yl)-2-butynyl]-2-pyrrolidinone hydrobromide, m.p. 178°-182° C.

1-[4-(5-methyl-1H-imidazol-1-yl)-2-butynyl]-2-pyrrolidinone

A portion of the salt was dissolved in water (2 mL) and partitioned between ethyl acetate (100 mL) and 4N sodium hydroxide solution (3.8 mL). Evaporation of the ethyl acetate gave a solid which was crystallized from ethyl acetate:ether (15 mL of 1:1) to give 1.62 g of 1-[4-(5-methyl-1H-imidazol-1-yl)-2-butynyl]-2-pyrrolidinone, m.p. 79°-82° C.

A portion of the free base was converted to the hydrochloride salt, m.p. 182°-184° C. from methanol:ether.

A portion of the free base was converted to the toluenesulfonate salt obtained as a monohydrate, m.p. 101°-107° C. from methanol:ether.

A portion of the free base was converted to the methanesulfonate salt, m.p. 127°-129° C. from methanol:ethylacetate.

A portion of the free base was converted to the hemioxalate salt, m.p. 194°-197° C. from methanol.

EXAMPLE 4

1-[4-(2,4-Dimethyl-1H-imidazol-1-yl)-2-butynyl]-2-pyrrolidinone (Compound 4)

The product was prepared according to Example 1, part B, by substituting 2,4-dimethylimidazole for imidazole. The product was obtained as a liquid. Chromatography on silica gel using chloroform:methanol as the eluant gave, as the first product eluted from the column, 1-[4-(2,4-dimethyl-1H-imidazolyl)-2-butynyl]-2-pyrrolidinone.

Continued elution of the column gave additional Compound 4 mixed with 1-[4-(2,5-dimethyl-1H-imidazolyl)-2-butynyl]-2-pyrrolidinone (7:3 mixture by GC).

EXAMPLE 5

1-[4-(1H-Imidazol-1-yl)-2-butynyl]-5-methyl-2-pyrrolidinone (Compound 5)

This product, a liquid, was prepared according to Example 1 by substituting 1[4-(diethylaminol)-2-butynyl]-5-methyl-2-pyrrolidinone for 1-[4-(diethylamino)-2-butynyl]-2-pyrrolidinone. The bulk of the product was converted to the oxalate salt m.p. 108°-110 C.

EXAMPLE 6

1-[4-(1H-Imidazol-1-yl)-2-butynyl]-1-methyl-2-pyrrolidinone (Compound 6)

This product, a liquid, was prepared according to Example 1 by substituting 1-[4-(diethylamino)-1-methyl-2-butynyl]-2-pyrrolidinone for 1-[4-(diethylamino)-2-butynyl]-2-pyrrolidinone. The bulk of the product was converted to the oxalate salt m.p. 103°-115° C.

EXAMPLE 7

1-[4-(2-Ethyl-1H-imidazol-1yl)-2-butynyl]-2-pyrrolidinone (Compound 7)

This product, a liquid, was prepared according to Example 1, part B, by substituting 2-ethylimidazole for imidazole. NMR δ 1.36 (t, 3H), 2.06 (m, 2H), 2.40, (t, 2H), 2.71 (q, 2H), 3.43 (t, 2H), 4.13 (s, 2H), 4.62 (m, 2H), 6.93 (s, 1H), and 6.95 (s, 1H).

EXAMPLE 8

1-[4-(2-Chloro-1H-imidazol-1-yl)-2-butynyl]-2-pyrrolidinone (Compound 8)

This product, a liquid, was prepared according to Example 1, part B, by substituting 2-chloro-1H-imidazole for imidazole.

EXAMPLE 9

1-[4-(4-Methyl-1H-imidazol-1-yl)-2-butynyl]-2-pyrrolidinone (Compound 9)

A mixture of 4-methylimidazole (17.4 g, 0.21 mol) and 1-(4-bromo-2-butynyl)-2-pyrrolidinone (11.4 g, 0.53 mol) in dioxane (250 mL) was stirred at room temperature for 24 hr. The solvent was removed under reduced pressure and the product was partitioned between ethyl acetate and 4N NaOH solution (5 mL). The ethyl acetate was removed and the residual oil was chromatographed on silica gel using chloroform as the initial eluant. Elution of the column with 2.5% methanol:chloroform gave 7.9 g of material.

Oxalic acid (1.65 g, 0.5 equiv) in methanol (30 mL) was added and the solution was cooled to −10° C. overnight. The precipitate was filtered off to give 2.98 g of 84% pure 1-[4-(5-methyl-1H-imidazol-1-yl)-2-butynyl]-2-pyrrolidinone hemioxalate. Recrystallization from methanol gave 2.43 g of 98% pure isomer, m.p. 194°-197° C.

A second crop of crystals, 5.05 g was obtained from the initial mother liquors, and these were recrystallized from methanol ether to give 3.29 g of 1-[4-(4-methyl-1H-imidazol-1-yl)-2-butynyl]-2-pyrrolidinone, hemioxalate m.p. 134°-137° C. (85% isomeric purity by GC).

EXAMPLE 10

1-[4-(1H-Imidazol-1-yl)-2-butynyl]-2,5-pyrrolidinedione (Compound 10)

This compound was prepared following Example 1, part B but substituting 1-(4-bromo-2-butynyl)-2,5-pyrrolidinedione for BPP. The crude product was converted to the free base which was purified by chromatography on silica gel to give the title compound, m.p. 120°-122° C.

EXAMPLE 11

1-[4-(5-Methyl-1H-imidazol-1-yl)-2-butynyl]-2,5-pyrrolidinedione (Compound 11)

This compound was prepared following Example 3 burt substituting 1-(4-bromo-2-butynyl)-2,5-pyrrolidinedione for BPP. The crude product was converted to the free base which was purified by chromatography on silica gel to give the title compound, m.-. 114°-117° C.

EXAMPLE 12

1-[4-(5-Methyl-1H-imidazol-1-yl)-1-methyl-2-butynyl]-2-pyrrolidinone hydrobromide) Compound 12)

This compound, m.p. 171°-174° C., was prepared following Example 3 but substituting 1-[4-bromo-1-methyl-2-butynyl)-2-pyrrolidinone for BPP.

EXAMPLE 13

1-[4-(5-methyl-2-pyrrolidinone (Compound 13)

This compound was prepared following Example 3 but substituting 1-[4-bromo-2-butynyl)-5-methyl-2-pyrrolidinone for BPP. The crude product was converted to the free base which was purified by chromatography on silica gel to give the title compound as a liquid.

EXAMPLE 14

N-[4-(1H-Imidazol-1-yl)-1-methyl-2-butynyl]-N-methylacetamide (Compound 14)

Part A

Cyanogen bromide (19.87 g, 0.19 mol) was added to a stirred solution of N-[4-(diethylamino)-1-methyl-2-butynyl]-N-methylacetamide (35.85 g, 0.17 mol) in dioxane (300 mL). After stirring at room temperature for 10 min, the solvent was removed under reduced pressure to give 49.64 g brown oil. The compound was purified by chromatography on silica gel in chloroform to give 31.71 g (85.3%) of N-(4-bromo-1-methyl-2-butynyl)-N-methylacetamide as a yellow oil and 6.86 g of a mixture of the desired product contaminated with N-[4-(N-cyano-N-ethylamino)-1-methyl-2-butynyl]-N-methylacetamide.

Part B

N-(4-Bromo-1-methyl-2-butynyl)-N-methylacetamide (3.0 g, 13.7 mmol) was added to a stirred solution of imidazole (2.8 g, 41.2 mmol) in THF (200 mL) at room temperature. After 3 days the THF was removed and the residual oil was partitioned between ethyl acetate and 4N NaOH. Evaporation of the ethyl acetate gave an oil which was chromatographed on silica gel to give 2.6 g of Compound 14 as an oil. NMR $\delta$ 1.31 (d, 2.5H), 1.45 (d, 0.5H), 2.09 (s, 2.5HL), 2.11, (s, 0.5H), 2.90 (s, 0.5H), 2.97 (s, 2.5H), 4.75 (s, 2H and m, 0.15H), 5.67 (s, 0.85H), 7.01 (s, 1H), 7.09 (s, 1H), and 7.58 (s, 1H).

EXAMPLE 15

N-[4-(2-Methyl-1H-imidazol-1-yl)-1-methyl-2-butynyl]-N-methylacetamide (Compound 15)

This liquid product was prepared according to the procedure in Example 14 by substituting 2-methylimidazole for imidazole. NMR $\delta$ 1.30 (d, 2.6H, 1.43 (d, 0.4H), 2.08 (s, 2.6H), 2.13 (s, 0.4H), 2.41 (s, 3H), 2.89 (s, 0.4H), 2.95 (s, 2.6H), 4.61 (s, 2H), 4.67 (m, 0.1H), 5.65 (s, 0.9H), 6.915 (s, 1H), and 6.925 (s, 1HL).

EXAMPLE 16

N-[4-(4,5-Dimethyl-1H-imidazol-1-yl)-1-methyl-2-butynyl]-N-methylacetamide Compound 16)

This liquid product was prepared according to the procedure in Example 14 by substituting 4,5-dimethylimidazole for imidazole. NMR $\delta$ 1.30 (d, 2.6H), 1.43 (d, 0.4H), 2.08 (s, 2.6H), 2.13 (s, 0.4H), 2.16 (s, 6H), 2.89 (s, 0.4H), 2.95 (s, 2.6H), 4.56 (m, 2H), 4.70 (m, 0.1H), 5.66 (s, 0.9H) and 7.42 (s, 1H).

EXAMPLE 17

N-[4-(2,4-Dimethyl-1H-imidazol-1-yl)-1-methyl-2-butynyl]-N-methylacetamide Compound 17) and N-[4-(2,5-Dimethyl-1H-imidazol-1-yl)-1-methyl-2butynyl]-N-methylacetamide (Compound 18)

These products, prepared according to the procedure in Example 14 by substituting 2,4-dimethylimidazole for imidazole, were obtained as a liquid. Chromatography on silica gel using chloroform:methanol as the eluant gave, as the first product eluted from the column, N-[4-(2,4-dimethyl-1H-imidazol-1-yl)-1-methyl-2-butynyl]-N-methylacetamide.

Repeated chromatography of the later fractions from the column gave N-[4-(2,5-dimethyl-1H-imidazol-1-yl)-1-methyl-2-butynyl]-N-methylacetamide.

EXAMPLE 18

N-[4-(1H-Imidazol-1-yl)-2-butynyl]-N-methylacetamide (Compound 19)

This compound was prepared following Example 1, part B, but substituting N-[4-bromo-2-butynyl]-N-methylacetamide for BPP. The crude product was converted to the free base which was purified by chromatography on silica gel to give the title compound as a liquid.

A portion of the product was converted to the sesquioxalate salt, m.p. 113°-115° C.

EXAMPLE 19

N-[4-(5-Methyl-1H-imidazol-1-yl)-2-butynyl]-N-methylacetamide (Compound 20)

This compound was prepared following Example 3, but substituting N-(4-bromo-2-butynyl)-N-methylacetamide for BPP. The crude product was converted to the free base which was purified by chromatography on silica gel to give the title compound as a liquid.

A portion of the product was converted to the hemioxalate salt, m.p. 170°-173° C.

EXAMPLE 20

N-[4(5-Methyl-1H-imidazol-1-yl)-1-methyl-2-butynyl]-N-methylacetamide (Compound 21)

This compound was prepared following Example 3 but substituting N-(4-bromo-1-methyl-2-butynyl)-N-methylacetamide for BPP. The crude product was converted to the free base which was purified by chromatography on silica gel to give the title compound as a liquid.

EXAMPLE 21

N-[4-(1H-Imidazol-1-yl)-2-butynyl]acetamide (Compound 22)

This compound was prepared following Example 1, part B, but substituting N-(4-bromo-2-butynyl)acetamide for BPP. The crude product was converted to the free base which was purified by chromatography on silica gel to give the title compound, m.p. 93°-95° C.

EXAMPLE 22

N-[4-(5-Methyl-1H-imidazol-1-yl)-2-butynyl]acetamide (Compound 23)

This compound was prepared following the procedure for Example 3, but substituting N-(4-bromo-2-butynyl)acetamide for BPP. The crude product was converted to the free base which was purified by chromatography on silica gel to give the title compound, m.p. 111°-115° C.

EXAMPLE 23

[4-(1H-Imidazol-1-yl)-2-butynyl]trimethyl urea (Compound 24)

This compound was prepared following Example 1, part B, but substituting (4-bromo-2-butynyl)trimethyl urea for BPP. The crude product was converted to the free base which was purified by chromatography on silica gel.

A portion of the product was converted to the oxalate salt, m.p. 130°-132° C.

EXAMPLE 24

[4-(5-Methyl-1H-imidazol-1-yl)-2-butynyl]trimethyl urea (Compound 25)

This compound was prepared following the procedure of Example 3, but substituting (4-bromo-2-butynyl)trimethyl urea for BPP. the crude product was converted to the free base which was purified by chromatography on silica gel to give the title compound as a liquid.

EXAMPLE 25

Methyl [4-(1H-imidazol-1-yl)-2-butynyl]methylcarbamate (Compound 26)

This compound was prepared following Example 1, part B, but substituting methyl [4-bromo-2-butynyl]methyl carbamate for BPP. The crude product was converted to the free base which was purified by chromatography on silica gel to give the title compound as a liquid. The bulk of the product was converted to the oxalate salt, mp 113°-115° C. from methanol:ether.

EXAMPLE 26

Methyl [4-(5-methyl-1H-imidazol-1-yl)-2-butynyl]methyl carbamate (Compound 27)

This compound was prepared following the procedure of Example 3 but substituting methyl [4-bromo-2-butynyl]methyl carbamate for BPP. The crude product was converted to the free base which was purified by chromatography on silica gel to give the title compound as a liquid. The salt of the product was converted to the oxalate salt mp 119°-121° C. from methanol:ether.

EXAMPLE 27

1-[4-(Pyrrolidinyl)-2-butynyl]-1H-imidazole (Compound 28)

Part A

A mixture of propargyl bromide (29.7 g, 0.2 mol) and imidazole (27.3 g, 0.40 mol) in dioxane (200 mL) was stirred at room temperature for 3 days. The solvent was removed under reduced pressure and the residual oil was partitioned between ethyl acetate (300 mL) and 4N NaOH solution (50 mL). The aqueous phase was separated and extracted twice with ethyl acetate. Evaporation of the ethyl acetate gave an oil which was chromatographed on silica gel using chloroform as the eluant to give 14.8 g of 1-(2-propynyl)-1H-imidazole as an oil.

Part B

A mixture of 1-(2-propynyl)-1H-imidazole (2.5 g, 0.023 mol), pyrrolidine (2.0 g, 0.026 mol), paraformaldehyde (0.85, 0.028 mol) and cuprous chloride (30 mg) in dioxane (20 mL) was heated at 50° C. for 4 h. The solvent was evaporated and the residual oil was dissolved in chloroform, filtered, and chromatographed on silica gel to give 2.99 g of 1-[4-(pyrrolidinyl)-2-butynyl]-1H-imidazole as an oil.

The bulk of the product was treated with oxalic acid (2.62 g) in methanol:ether to give 3.11 g of the dioxalate salt as a hemihydrate, m.p. 94°-97° C. The analytical sample was recrystallized from methanol:ether; m.p. 97°-99° C.

EXAMPLE 28

4-(1H-Imidazol-1-yl)-N,N-dimethyl-2-butyn-1-amine (Compound 29)

This product, prepared according to the procedure of Example 27 by substituting dimethylamine for pyrrolidine, was obtained as a liquid.

The bulk of the product was converted to the dioxalate salt, m.p. 160°-162° C. from methanol:ether.

EXAMPLE 29

2-Methyl-1-[4-(pyrrolidinyl)-2-butynyl]-1H-imidazole (Compound 30)

This product, prepared according to the procedure of Example 27 by substituting 2-methylimidazole for imidazole, was obtained as a liquid.

The bulk of the product was converted to the dimaleate salt, m.p. 119°-122° C. from methanol.

EXAMPLE 30

N,N-Diethyl-4-(1H-Imidazol-1-yl)-2-butyn-1-amine (Compound 31)

This product, prepared according to the procedure of Example 4 by substituting diethylamine for pyrrolidine, was obtained as a liquid.

The bulk of the product was converted to the sesquioxalate salt, obtained as a hemihydrate, m.p. 109°-112° C. from methanol.

EXAMPLE 31

5-Methyl-1[(4-pyrrolidinyl)-2-butynyl]-1H-imidazole Compound 32))

Part A

Following the procedure of Example 3, but substituting propargyl bromide for BPP, there was obtained 5-methyl-1-(2-propynyl)imidazole hydrobromide, m.p. 178°-180° C.

Part B

The compound 28, a liquid, was obtained following the procedure of Example 27, but substituting 5-methyl-1-(2-propynyl)imidazole for 1-(2-propynyl)imidazole.

A portion of the product was converted to the sesquioxalate salt, m.p. 117°-119° C.

TABLE 1

| Compound | CNS Id (ED$_{50}$) mg/kg) HCl Writh. Protect | CNS Cholinergic Receptor Binding Assays | | Oxot. Antagonist Tremor |
|---|---|---|---|---|
| | | Ki (nM) QNB | Ki (nM) Oxotremorine | |
| Oxotremorine | .025 | 220.0 | 0.4 0.5 | 0.11 |
| Oxotremorine 5 | 11 | 14.0 14.0 | 1.4 1.5 | 1.73 |
| ① | .4 | 600.0 | 1.3 | >100 |
| ② | 0.1 | 3.8 | 0.3 | >100 |
| ③ | 2.6 | 64.0 79.8 | 3.2 3.3 | >100 >10 |
| ④ | >50 | 160.0 | 68.0 | 54 |
| ⑤ | >50 | 171.2 | 23.00 | 20.9 |
| ⑥ | >50 | 565.9 | 33.5 | 45 |
| ⑦ | | | | |

TABLE 1-continued
| Compound | CNS Id (ED$_{50}$ mg/kg) HCl Writh. Protect | CNS Cholinergic Receptor Binding Assays | | Oxot. Antagonist Tremor |
| --- | --- | --- | --- | --- |
| | | Ki (nM) QNB | Ki (nM) Oxotremorine | |
| 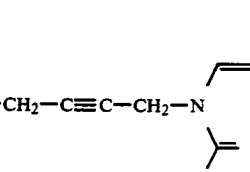 | >50 | 56.9 | 29.1 | 9.7 |
| ⑧ 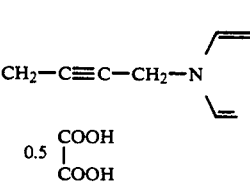 | — | >10000 | 577 | >100 |
| ⑨ 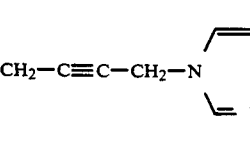 | — | 377.0 | 10.3 | >100 |
| ⑩ 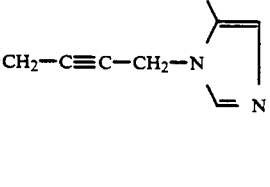 | — | 633.8 | 23.5 | 25 |
| ⑪ 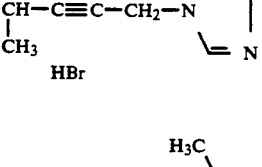 | — | 100.5 | 10.3 | 37 |
| ⑫ 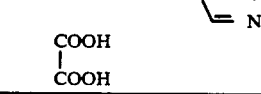 | — | 16.8 | 5.2 | 25 |
| ⑬  | — | 11.6 | 1.7 | 14 |

TABLE 2

| Compound | CNS Id (ED$_{50}$ mg/kg) HCl Writh. Protect | CNS Cholinergic Receptor Binding Assays | | Oxot. Antagonist Tremor |
| --- | --- | --- | --- | --- |
| | | Ki (nM) QNB | Ki (nM) Oxotremorine | |
| BM-5 | 4.4 | 26 | 0.9 | 3.7 |
| (14) H$_3$C—C(=O)—N(CH$_3$)—CH(CH$_3$)—C≡C—CH$_2$—N(pyrazine) | 0.9 | 1500.0 | 12.0 | >100 |
| (15) CH$_3$—C(=O)—N(CH$_3$)—CH(CH$_3$)—C≡C—CH$_2$—N(2-methylpyrazine) | >50 | 19.0 | 1.6 | 11.8 |
| (16) CH$_3$—C(=O)—N(CH$_3$)—CH(CH$_3$)—C≡C—CH$_2$—N(2,3-dimethylpyrazine) | >50 | 79.0 | 42.0 | 25.4 |
| (17) CH$_3$—C(=O)—N(CH$_3$)—CH(CH$_3$)—C≡C—CH$_2$—N(2,5-dimethylpyrazine) | >50 | 180.0 | 130.0 | 80 |
| (18) CH$_3$—C(=O)—N(CH$_3$)—CH(CH$_3$)—C≡C—CH$_2$—N(2,6-dimethylpyrazine) | — | 8.50 | 6.30 | 14.2 |
| (19) CH$_3$—C(=O)—N(CH$_3$)—CH$_2$—C≡C—CH$_2$—N(pyrazine) · 1.5 (COOH)$_2$ | — | >10000 | 1.9 | >100 |
| (20) CH$_3$—C(=O)—N(CH$_3$)—CH$_2$—C≡C—CH$_2$—N(2-methylpyrazine) · 0.5 (COOH)$_2$ | — | 172.0 | 3.6 | >100 |
| (21) CH$_3$—C(=O)—N(CH$_3$)—CH(CH$_3$)—C≡C—CH$_2$—N(3-methylpyrazine) | — | 184.3 | 10.0 | 80 |
| (22) | | | | |

TABLE 2-continued

| Compound | CNS Id (ED$_{50}$ mg/kg) HCl Writh. Protect | CNS Cholinergic Receptor Binding Assays | | Oxot. Antagonist Tremor |
|---|---|---|---|---|
| | | Ki (nM) QNB | Ki (nM) Oxotremorine | |
| H$_3$C—C(O)—NH—CH$_2$—C≡C—CH$_2$—N(pyrazole) | — | >10000 | 186.9 | >100 |
| ㉓ H$_3$C—C(O)—NH—CH$_2$—C≡C—CH$_2$—N(CH$_3$-pyrazole) | — | >10000 | 213.4 | >100 |
| ㉔ (H$_3$C)$_2$N—C(O)—N(CH$_3$)—CH$_2$—C≡C—CH$_2$—N(pyrazole) · COOH-COOH | — | 10000.0 | 34.0 | >100 |
| ㉕ (H$_3$C)$_2$N—C(O)—N(CH$_3$)—CH$_2$—C≡C—CH$_2$—N(CH$_3$-pyrazole) | — | 10000.0<br>10000.0 | 82.1<br>82.1 | >100 |
| ㉖ CH$_3$O—C(O)—N(CH$_3$)—CH$_2$—C≡C—CH$_2$—N(pyrazole) · COOH-COOH | — | 10000.0 | 120.0 | >100 |
| ㉗ CH$_3$O—C(O)—N(CH$_3$)—CH$_2$—C≡C—CH$_2$—N(CH$_3$-pyrazole) · COOH-COOH | — | 10000.0 | 200.0 | >100 |

TABLE 3

| Compound | CNS Id (ED$_{50}$ mg/kg) HCl Writh. Protect | CNS Cholinergic Receptor Binding Assays | | Oxot. Antagonist Tremor |
|---|---|---|---|---|
| | | Ki (nM) QNB | Ki (nM) Oxotremorine | |
| Tremorine | | 4600.0 | 370.0 | >100 |
| ㉘ (pyrazole)N—CH$_2$—C≡C—CH$_2$—N(pyrrolidine) · 2 COOH-COOH · 0.5 H$_2$O | 3.1 | 10000.0 | 1900.0 | >100 |
| ㉙ | | | | |

TABLE 3-continued

| Compound | CNS Id (ED$_{50}$ mg/kg) HCl Writh. Protect | CNS Cholinergic Receptor Binding Assays Ki (nM) QNB | Ki (nM) Oxotremorine | Oxot. Antagonist Tremor |
|---|---|---|---|---|
| (structure with pyridine, N-CH$_2$-C≡C-CH$_2$-N(CH$_3$)$_2$, 2 oxalate) | >50 | 10000.0 / 10000.0 | 10000.0 / 10000.0 | >100 |
| ㉚ (structure with methylimidazoline, N-CH$_2$-C≡C-CH$_2$-N-pyrrolidine, 2 maleate) | 5 | 7700.0 | 620.0 | >100 |
| ㉛ (structure with pyridine, N-CH$_2$-C≡C-CH$_2$-N(CH$_2$CH$_3$)$_2$, 1.5 oxalate · 0.5 H$_2$O) | >50 | 10000.0 | 10000.0 | >100 |
| ㉜ (structure with pyrrolidine, N-CH$_2$-C≡C-CH$_2$-N-methylimidazole, 1.5 oxalate) | | 10000.0 | 435.6 | >100 |

FORMULAS

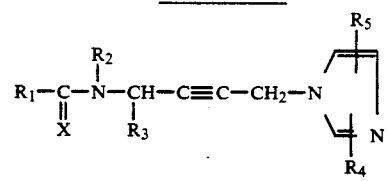

I 45

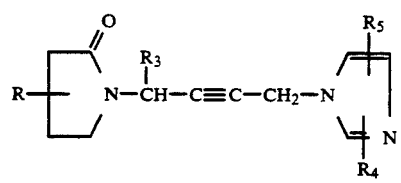

i 50

-continued
FORMULAS

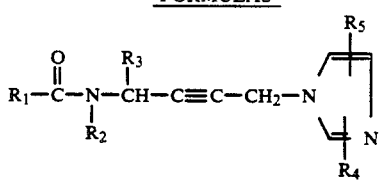

ii

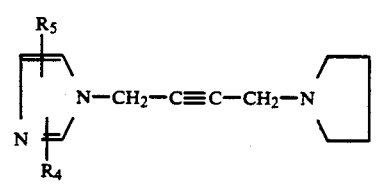

iii 55

SCHEME 1

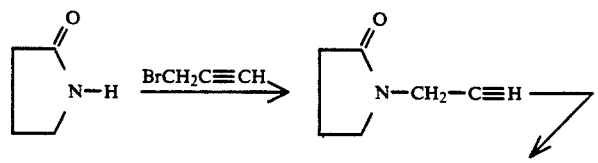

SCHEME 1
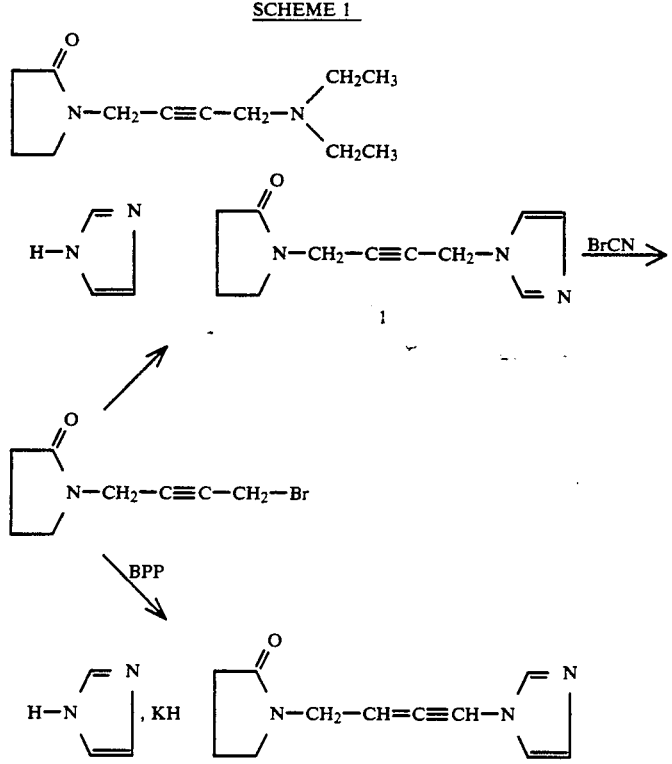
SCHEME 2
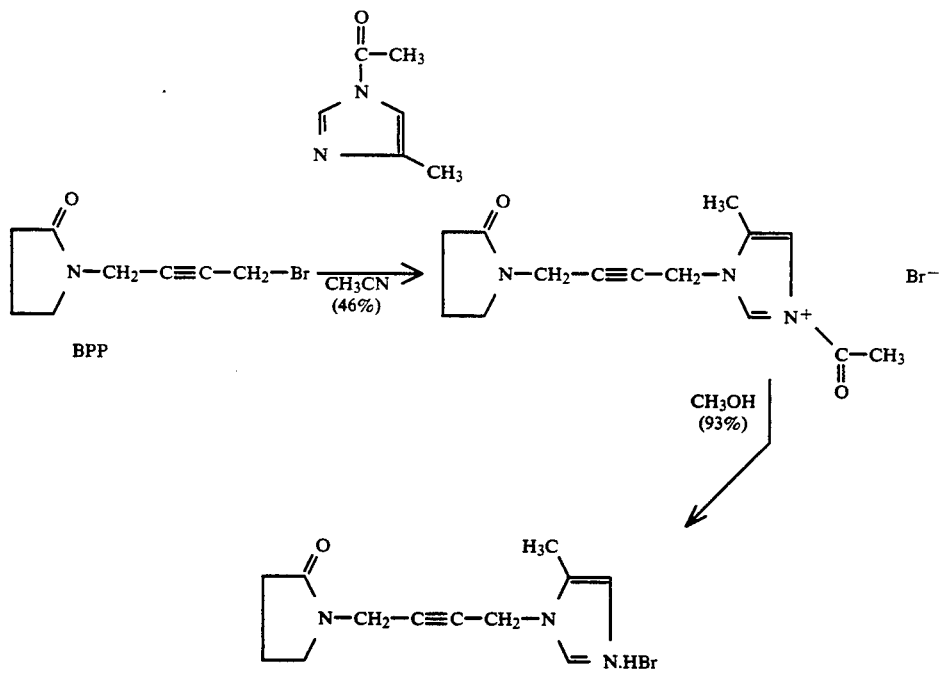
SCHEME 3

SCHEME 3

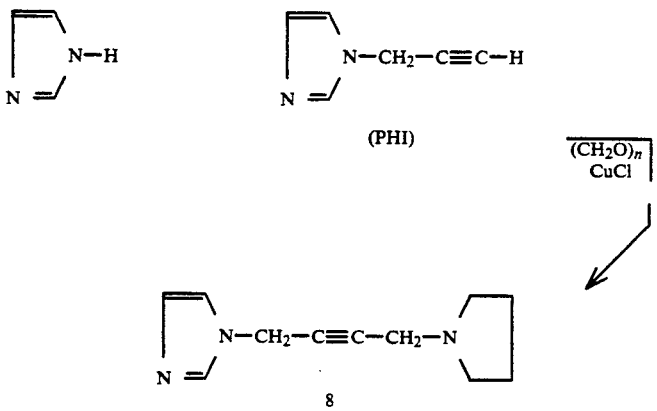

(PHI)

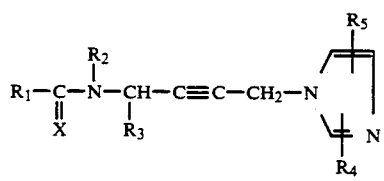

We claim:
1. A compound of the following structural formula:

R₁—C(=X)—N(R₂)—CH(R₃)—C≡C—CH₂—N(R₅)(R₄) [ring]

or a therapeutically acceptable salt thereof;
wherein X is H₂ or O;
R₁ is hydrogen, methyl, ethyl, methylamino, dimethylamino, methoxy or ethoxy;
R₂ is hydrogen, methyl or ethyl or R₁ and R₂ are joined to form a 5 or 6 member cyclic ring which can be methyl or carbonyl substituted; and
R₃, R₄m and R₅ are independently chosen from hydrogen, methyl, ethyl, fluorine, chlorine, bromine or iodine.

2. The compound of claim 1, wherein said R₁ and R₂ substituents are joined to form a pyrrolidine, pyrrolidinone, piperidine or piperidinone ring.

3. The compound of claim 1 wherein R₁ and R₂ are joined to form a pyrrolidine ring, R₃ and R₄ are independently hydrogen or methyl and R₅ is hydrogen.

4. The compound of claim 3 which is:

a) 1[4-(1-pyrrolidinyl)-2-butynyl]-1H-imidazole; or
b) 2-methyl-1[4-(1-pyrrolidinyl)-2-butynyl]-1H-imidazole.

5. The compound of claim 1 wherein R₁ and R₂ form a pyrrolidinone ring, R₃ and R₄ are independently hydrogen or methyl and R₅ is hydrogen.

6. The compound of claim 5 which is:

a) 1-(4-(1H-imidazol-1-yl)-2-butynyl)-2-pyrrolidinone;
b) 1-[4-(2-methyl-1H-imidazol-1-yl)-2-butynyl]-2-pyrrolidinone;
c) 1-[4-(5-methyl-1H-imidazol-1-yl)-2-butynyl]-2-pyrrolidinone;
d) 1-[4-(2,4-dimethyl-1H-imidazol-1-yl)-2-butynyl-2-pyrrolidinone;
e) 1-[4-(2-ethyl-1H-imidazol-1-yl)-2-butynyl]-2-pyrrolidinone;
f) 1-[4-(1H-imidazol-1-yl)-1-methyl-2-butynyl]-2-pyrrolidinone;
g) 1-[4-(4-methyl-1H-imidazol-1-yl)-2-butynyl]-2-pyrrolidinone;
h) 1-[4-(5-methyl-1H-imidazol-1-yl)-1-methyl-2-butynyl]-2-pyrrolidinone.

7. The compound of claim 1 wherein said R₁ and R₂ are joined to form a pyrrolidinone ring substituted with a methyl group or an additional carbonyl group.

8. The compound of claim 7 which is:

a) 1-[4-(1H-Imidazol-1-yl)-2-butynyl]-5-methyl-2-pyrrolidinone;
b) 1-[4-(1H-imidazol-1-yl)-2-butrynyl]-2,5-pyrrolidinedione;
c) 1-[4-(5-methyl-1H-imidazol-1-yl)-2-butynyl]-2,5-pyrrolidinedione;
d) 1-[4-(5-methyl-1H-imidazol-1-yl)-2-butynyl]-5-methyl-2-pyrrolidinone.

9. The compound of claim 1 wherein R₁ is methyl, R₂, R₃, R₄ and R₅ are independently hydrogen or methyl and X is oxygen.

10. The compound of claim which is:

a) N-[4-(1H-imidazol-1-yl)-1-methyl-2-butynyl]-N-methylacetamide;
b) N-methyl-N-[1-methyl-4-(2-methyl-1H-imidazol-1-yl)-2-butynyl]acetamide;
c) N-[4-(4,5-dimethyl-1H-imidazol-1-yl)-1-methyl-2-butynyl]-N-methylacetamide;
d) N-[4-(2,4-dimethyl-1H-imidazol-1-yl)-1-methyl-2-butynyl]-N-methylacetamide;
e) N-[4-(2,5-dimethyl-1H-imidazol-1-yl)-1-methyl-2-butynyl]-N-methylacetamide;
f) N-[4-(5-methyl-1H-imidazol-1-yl)-2-butynyl]-N-methylacetamide;
g) N-[4-(5-methyl-1-imidazol-1-yl)-1-methyl-2-butynyl]-N-methylacetamide;
h) N-[4-(1H-imidazol-1-yl)-2-butynyl]acetamide;
i) N-[4-(5-methyl-1H-imidazol-1yl)-2-butynyl]acetamide; or
j) N-[4-(1H-imidazol-1-yl-2-butynyl]-N-methylacetamide.

11. A compound of the following structural formula:

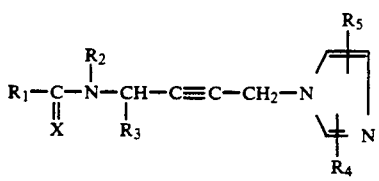

or a therapeutically acceptable salt thereof;
wherein X is $H_2$ or O;
$R_1$ is hydrogen, methyl, ethyl, methylamino, dimethylamino, methoxy or ethoxy;
$R_2$ is hydrogen, methyl or ethyl or $R_1$ and $R_2$ are joined to form a 5 or 6 member cyclic ring which can be methyl or carbonyl substituted;
$R_3$ and $R_4$ are independently chosen from hydrogen, methyl, ethyl, fluorine, chorine, bromine or iodine; and
wherein $R_5$ is chlorine or bromine.

12. The compound of claim 11 wherein $R_1$ is dimethylamino or methoxy.

13. The compound of claim 12 which is:

a) [4-(1H-imidazol-1-yl)-2-butynyl]trimethyl urea;
b) [4-(5-methyl-1H-imidazol-1-yl)-2-butynyl]trimethyl urea;
c) Methyl[4-(imidazol-1-yl)-2-butynyl]methylcarbamate; or
d) Methyl [4-(5-methyl-1H-imidazol-1-yl)-2-butynyl]-methyl carbamate.

14. A method for treating pain, mental deficiencies, extrapyramidal motor disorders, glaucoma or parasympathetic nervous system disorders in animal or human hosts comprising:

administering a pharmaceutically effective amount of a compound structurally represented by the formula:

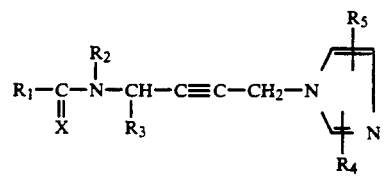

or a therapeutically acceptable salt thereof;
wherein X is $H_2$ or O;
$R_1$ is hydrogen, methyl, ethyl, methylamino, dimethylamino, methoxy or ethoxy;
$R_2$ is hydrogen, methyl or ethyl or $R_1$ and $R_2$ are joined to form a 5 or 6 member cyclic ring which can be methyl or carbonyl substituted, $R_3$, $R_4$ and $R_5$ are independently chosen from hydrogen, methyl or ethyl or a halogen.

15. The method of claim 11 wherein said $R_1$ and $R_2$ substituents form a puyrrolidine, pyrrolidinone, piperidine or piperidinone ring.

16. The compound of claim 1 which is 5-methyl-1-(4-(1-pyrrolidinyl)-2-butynyl)-1H-imidazole.

* * * * *